(12) United States Patent
Moser et al.

(10) Patent No.: US 11,079,218 B2
(45) Date of Patent: Aug. 3, 2021

(54) MEASURING DISTANCE USING A LASER PROCESSING SYSTEM WITH OPTICAL AMPLIFIER FOR AMPLIFYING MEASURING BEAM OR REFLECTED PART OF MEASUREMENT BEAM

(71) Applicant: PRECITEC GMBH & CO. KG, Gaggenau (DE)

(72) Inventors: Rüdiger Moser, Malsch (DE); Martin Schönleber, Aschaffenburg (DE)

(73) Assignee: PRECITEC GMBH & CO. KG, Gaggenau (DE)

( * ) Notice: Subject to any disclaimer, the term of this patent is extended or adjusted under 35 U.S.C. 154(b) by 56 days.

(21) Appl. No.: 16/255,472

(22) Filed: Jan. 23, 2019

(65) Prior Publication Data
US 2019/0226832 A1 Jul. 25, 2019

(30) Foreign Application Priority Data

Jan. 24, 2018 (DE) ...................... 10 2018 101 554.2

(51) Int. Cl.
*G01B 11/22* (2006.01)
*G01B 9/02* (2006.01)
(Continued)

(52) U.S. Cl.
CPC ............ *G01B 11/22* (2013.01); *B23K 26/032* (2013.01); *B23K 26/24* (2013.01); *B23K 26/705* (2015.10);
(Continued)

(58) Field of Classification Search
CPC ................ G01B 9/02091; G01B 11/22; G01B 9/02044; B23K 26/705; B23K 26/03; B23K 26/24; A61B 5/0066
See application file for complete search history.

(56) References Cited

U.S. PATENT DOCUMENTS 6,538,815 B1 * 3/2003 Cao .................. G02B 6/272
359/484.05
6,591,025 B1 * 7/2003 Siems .................. G01H 3/005
385/12

(Continued)

FOREIGN PATENT DOCUMENTS

DE 102 07 535 A1 9/2003
DE 10 2007 016 444 A1 10/2008
(Continued)

OTHER PUBLICATIONS

German Patent and Trademark Office, Office Action, DE Patent Application No. 10 2018 101 554.2, dated Jan. 17, 2019, eight pages (with concise explanation of relevance).

(Continued)

*Primary Examiner* — Michael P LaPage
(74) *Attorney, Agent, or Firm* — Fenwick & West LLP

(57) ABSTRACT

The present disclosure concerns a device for distance measurement for a laser processing system. The device comprises a light source, which is configured to generate a primary beam for direction onto a workpiece, at least one detection device configured to record a secondary beam reflected from the workpiece, at least one optical amplifier configured to amplify the primary beam and/or the secondary beam, and an evaluation unit configured to evaluate interference between spectral components in the frequency domain.

10 Claims, 9 Drawing Sheets

(51) Int. Cl.
*H01S 3/10* (2006.01)
*B23K 26/03* (2006.01)
*G02B 27/10* (2006.01)
*B23K 26/70* (2014.01)
*B23K 26/24* (2014.01)
*A61B 5/00* (2006.01)

(52) U.S. Cl.
CPC ..... *G01B 9/02044* (2013.01); *G01B 9/02091* (2013.01); *G02B 27/10* (2013.01); *H01S 3/10023* (2013.01); *A61B 5/0066* (2013.01)

(56) References Cited

U.S. PATENT DOCUMENTS

| | | | |
|---|---|---|---|
| 8,822,875 B2 | 9/2014 | Webster et al. | |
| 2003/0184758 A1* | 10/2003 | Bjarklev | G01N 21/4795 356/479 |
| 2011/0109911 A1* | 5/2011 | Podoleanu | G01B 9/02002 356/451 |
| 2012/0138586 A1 | 6/2012 | Webster et al. | |
| 2012/0285936 A1* | 11/2012 | Urashima | G01B 9/02069 219/121.63 |
| 2014/0233958 A1* | 8/2014 | Hulsey | G02B 26/0858 398/93 |
| 2015/0109605 A1* | 4/2015 | Major, Jr. | G01S 7/499 356/28 |
| 2017/0120337 A1* | 5/2017 | Kanko | B23K 26/032 |
| 2019/0049232 A1* | 2/2019 | Vakoc | A61B 5/0066 |

FOREIGN PATENT DOCUMENTS

| | | | |
|---|---|---|---|
| DE | 10 2010 016 862 B3 | 9/2011 | |
| DE | 10 2013 008 269 A1 | 11/2014 | |
| DE | 10 2013 015 656 A1 | 3/2015 | |
| DE | 10 2016 005 021 A1 | 9/2016 | |
| DE | 10 2015 007 142 A1 | 12/2016 | |
| DE | 10 2015 015 112 A1 | 5/2017 | |
| DE | 10 2015 015 330 A1 | 6/2017 | |
| EP | 1 977 850 A1 | 10/2008 | |
| WO | WO 02/21074 A2 | 3/2002 | |
| WO | WO-2008029506 A1 * | 3/2008 | ........ A61B 5/0073 |
| WO | WO 2014/138939 A1 | 9/2014 | |
| WO | WO 2015/039741 A1 | 3/2015 | |
| WO | WO 2016/062636 A1 | 4/2016 | |

OTHER PUBLICATIONS

PCT International Search Report and Written Opinion, PCT Application No. PCT/EP2018/086656, dated May 3, 2019, 14 pages (with concise explanation of relevance).

Zhao, Y. et al., "Enhancement of optical coherence microscopy in turbid media by an optical parametric amplifier," J. Biophotonics, vol. 8, No. 6, Sep. 5, 2014, pp. 512-521.

* cited by examiner (a)

(b)

MEASURING DISTANCE USING A LASER PROCESSING SYSTEM WITH OPTICAL AMPLIFIER FOR AMPLIFYING MEASURING BEAM OR REFLECTED PART OF MEASUREMENT BEAM

CROSS REFERENCE TO RELATED APPLICATION

This application claims priority under 35 U.S.C. § 119(a) to German patent application no. 10 2018 101 554.2 filed on Jan. 24, 2018, which is incorporated by reference herein in its entirety.

BACKGROUND

The present disclosure concerns a device and a method for distance measurement for a laser processing system, in particular for determining a depth of a vapour capillary (keyhole) in laser welding, and concerns a laser processing system, such as a system for material processing by means of a laser beam, such as, for example, a laser processing head for laser cutting or laser welding. The present disclosure concerns in particular a laser welding head with an optical coherence tomograph.

In material processing by means of a laser beam, such as laser welding or laser cutting, the laser beam emitted from a laser light source, such as the end of a laser conductive fibre, is focused onto the workpiece to be processed with the aid of beam guidance and focusing optics. A laser processing head with collimator optics and focusing optics is used as standard, wherein the laser light is supplied via an optical fibre, also designated as a laser source. In a device for material processing by means of a laser, e.g. a laser processing head, the laser light passes through a multiplicity of optical elements, such as lenses.

In a laser deep welding process, a vapour capillary, also known as a "keyhole", is formed during a welding process along the beam axis of the processing beam, and is surrounded by liquid melt. The depth of the keyhole is related to the welding depth, that is to say, to the depth to which the metal has been melted during the welding process. This depth is of great interest: On the one hand, it contains information about the strength of the welded joint (that is to say, whether the weld is sufficiently deep); on the other hand, knowledge of the depth ensures that the weld seam is not visible on the underside (that is to say, there is no undesired penetration welding). In addition to measuring the capillary depth, the surface of the workpiece in the region around the keyhole can also be recorded (topography measurements). Thus, for example, the seam can be located immediately before the welding process or the quality of the seam bead can be measured immediately after the welding process.

To determine the depth of the keyhole, that is to say, the welding depth, a measuring beam can be used which is directed into the keyhole. Here this takes the form of an optical measurement method, wherein the measurement is based on the back reflection of light from the end of the keyhole. Since the keyhole is usually small in diameter and very pointed, the measuring light in the keyhole is reflected very poorly, so that very little light is reflected back from the object arm of the interferometer. In particular, at high feed rates the keyhole is also strongly curved.

SUMMARY

It is an object of the present disclosure to provide a device and a method for distance measurement for a laser processing system, together with a laser processing system, in particular a system for material processing by means of a laser beam, such as a laser processing head or a system for laser cutting or laser welding, which enable a distance measurement, such as a depth measurement of the keyhole, together with a topography measurement in the lead-in zone and/or lead-out zone, with high precision.

This object is achieved by means of the subject matter of the independent claims. Advantageous configurations of the invention are specified in the dependent claims.

In accordance with the embodiments of the present disclosure, a distance-measuring device is specified for a laser processing system, in particular for a laser welding head, or a processing head for laser welding. The device comprises a light source configured to generate a primary beam for directing onto a workpiece, at least one detection device configured to record a secondary beam reflected from the workpiece, at least one optical amplifier configured to amplify the primary beam and/or the secondary beam, and an evaluation unit that is configured to evaluate interference between spectral components in the frequency domain. In particular, the evaluation unit may be configured to determine the depth of a keyhole created during a laser processing process. The device may comprise an optical coherence tomograph, such as a frequency domain coherence tomograph, or a Fourier domain coherence tomograph.

Preferred optional embodiments and particular aspects of disclosure ensue from the dependent claims, the figures and the present description.

The light source preferably comprises a light source with a broadband spectrum, e.g. at least one superluminescent diode (SLD), or a supercontinuum source. The evaluation unit may be configured to use spectral domain coherence tomography (spectral domain OCT) for the evaluation. Alternatively, a monochrome light source with a periodically tuned wavelength may be used (swept source OCT), preferably with a semiconductor-based optical amplifier to amplify the primary light.

The at least one optical amplifier is preferably a fibre amplifier, a semiconductor-based amplifier, a Raman amplifier, an optical parametric amplifier, a bi-directional amplifier, or a combination of these.

The distance-measuring device preferably comprises a splitting device for splitting the primary beam into a multiplicity of primary beams. The splitting device may comprise at least one multi-core fibre and/or a micro-lens arrangement. The splitting device is preferably configured to split the primary beam, in particular the amplified primary beam, into a multiplicity of primary beams. The multiplicity of primary beams may then be directed onto the workpiece so that at least one of the primary beams hits the keyhole, despite fluctuations in the keyhole. By this means the number, or yield, of valid measurement results for determining the distance to the floor of the keyhole may be increased. The splitting into a multiplicity of primary beams may be achieved by using a multi-core fibre that has a plurality of channels. Alternatively, the primary beam, in particular the amplified primary beam, may be fanned out, e.g. by means of a lens, and then bundled into the multiplicity of primary beams by means of a micro-lens arrangement.

The light source and the at least one optical amplifier are preferably arranged sequentially, so that the primary beam is directed into the at least one optical amplifier. For example, the at least one optical amplifier is arranged in the beam path of the primary beam such that the primary beam is directed directly into the at least one optical amplifier.

The at least one optical amplifier is preferably arranged in a beam path common to the primary beam and the secondary beam. The device comprises, for example, at least one circulator, which is configured so as to provision two or a plurality of beam paths for the primary beam and the secondary beam. The at least one circulator may be arranged so as to direct the primary beam into the at least one optical amplifier, and to direct the secondary beam towards the detection device.

The at least one circulator preferably comprises a first circulator and a second circulator, wherein the at least one optical amplifier is arranged between the first circulator and the second circulator. For example, between the first circulator and the second circulator, a first beam path may be provided for the primary beam, and a second beam path for the secondary beam.

The at least one optical amplifier is preferably arranged in the first beam path or in the second beam path.

The at least one optical amplifier preferably comprises a first optical amplifier and a second optical amplifier, wherein the first optical amplifier is arranged in the first beam path, and the second optical amplifier is arranged in the second beam path.

The at least one optical amplifier is preferably a bi-directional optical amplifier.

The device is preferably an optical coherence tomograph, and comprises a beam splitter to provision an object arm and a reference arm, wherein the at least one optical amplifier is arranged in a beam path of the object arm.

The device preferably comprises at least one circulator, which is configured so as to provision two or a plurality of beam paths for the primary beam and the secondary beam, wherein the at least one circulator is arranged in the beam path of the object arm. The at least one optical amplifier is, for example, arranged between the at least one circulator and the detection device, or is arranged between the beam splitter and the at least one circulator. In a further example, the at least one optical amplifier comprises a first optical amplifier and a second optical amplifier, wherein the first optical amplifier is arranged between the at least one circulator and the detection device, and wherein the second optical amplifier is arranged between the beam splitter and the at least one circulator.

The at least one optical amplifier is preferably arranged in the beam path of the secondary beam such that the secondary beam is directed towards the detection device.

The at least one detection device preferably comprises a first detection device and a second detection device, wherein the device further comprises a first beam splitter and a second beam splitter, wherein the first beam splitter is configured so as to provision an object arm and a reference arm, and wherein the second beam splitter is configured to direct at least a fraction of the secondary beam into the first detection device. The second beam splitter may, for example, be arranged in the beam path of the primary beam, or may be arranged in the reference arm.

The device preferably comprises a circulator, which is configured so as to provision two or a plurality of beam paths for the primary beam and the secondary beam, wherein the circulator is arranged between the at least one optical amplifier and the first beam splitter, and wherein the circulator is configured to direct at least a fraction of the secondary beam into the second detection device.

In accordance with further embodiments of the present disclosure, a laser processing system, or more particularly a laser processing head for laser welding, is specified. The laser processing system, or more particularly the laser processing head for laser welding, comprises the distance-measuring device in accordance with the embodiments described here.

In accordance with other embodiments, a distance-measurement method for a laser processing system is specified. The method comprises the direction of a primary beam onto a workpiece, the direction of a secondary beam from the workpiece to a detection device, an optical amplification of the primary beam and/or the secondary beam, and an evaluation of interference between spectral components in the frequency domain.

The method preferably further comprises the determination of a depth or a depth profile of a keyhole on the workpiece, and/or a topography of the workpiece, using the secondary beam reflected from the workpiece.

In accordance with the invention an additional element, namely the optical amplifier, is introduced into the beam path so as to amplify the primary beam, the secondary beam, or both beams optically. This enables a low-power broadband light source to be used for FD-OCT ("Fourier domain optical coherence tomography" or "optical coherence tomography in the frequency domain"), whereby the depth of a vapour capillary may be determined reliably and with high precision. By virtue of the optical amplification, even deeper vapour capillaries may in particular be measured.

In accordance with further embodiments of the present disclosure, a distance-measuring device for a laser processing system is specified. The device comprises a supercontinuum source, which is configured to generate a primary beam to be directed onto a workpiece, at least one detection device, which is configured to record a secondary beam reflected from the workpiece, and an evaluation unit, which is configured to evaluate interference between spectral components in the frequency domain. In addition to the amplification of broadband light sources, alternative broadband light sources may also be used with this equipment, which emit high light outputs without amplification, such as supercontinuum sources. These are based on the exploitation of non-linear effects in fibres, which are caused by short and intense laser pulses. Here average power outputs in the watt range, and pulse peak power outputs in the kW range, may be achieved.

BRIEF DESCRIPTION OF THE FIGURES

Examples of embodiments of the disclosure are shown in the figures and are described in more detail below. Here.

DETAILED DESCRIPTION OF EMBODIMENTS

In what follows, unless otherwise indicated, the same reference symbols are used for identical elements, and elements with the same function.

Figure 1:
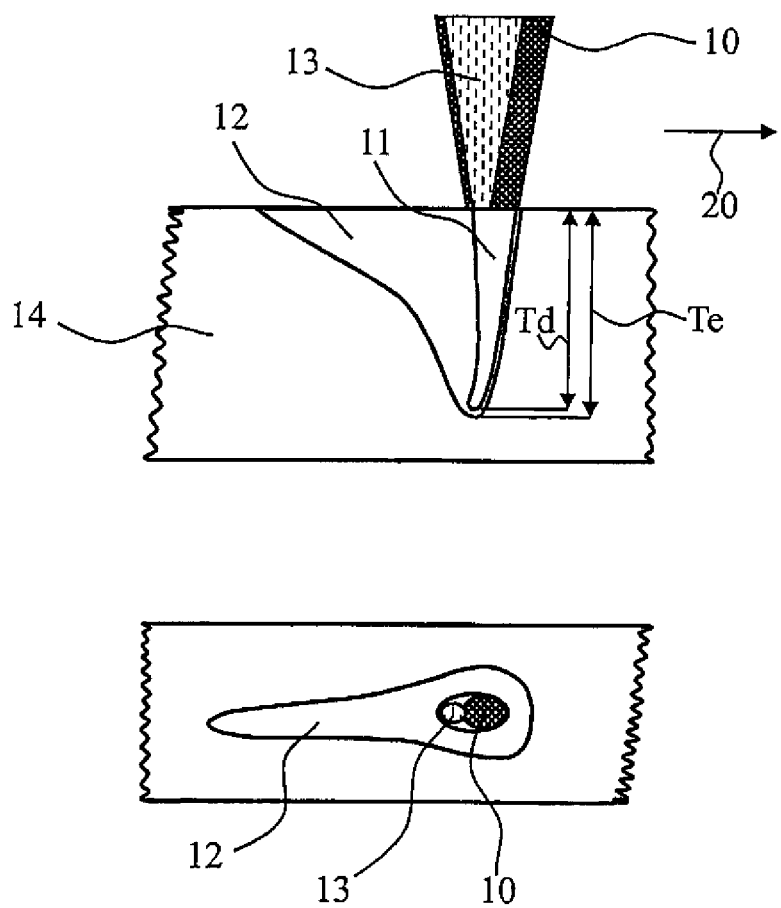
FIG. 1 shows a schematic cross-sectional view of a workpiece (above) and a plan view of the workpiece (below), representing a keyhole and a measuring beam during welding in accordance with embodiments of the present disclosure.
Figure 2:
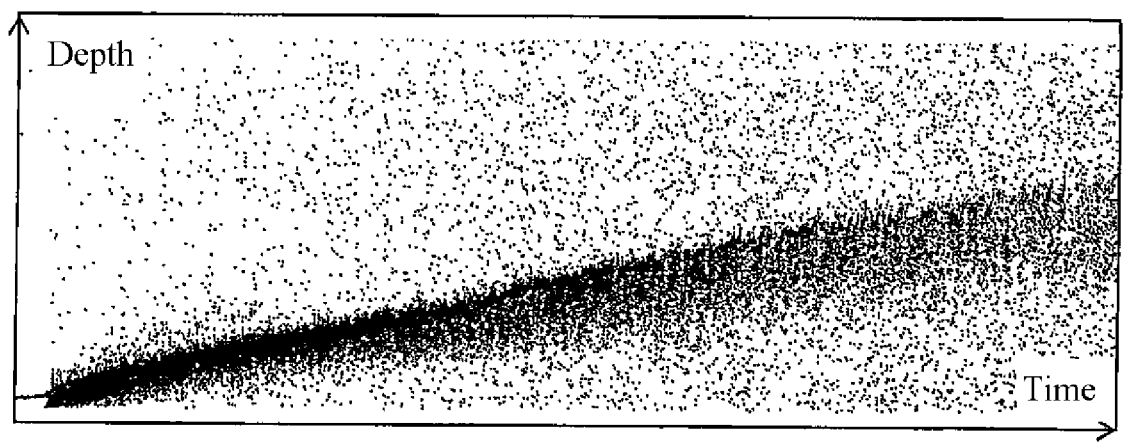
FIG. 2 shows distance values (raw data) from a vapour capillary of an optical coherence tomograph.

FIG. 1 shows a schematic cross-sectional view of a workpiece (above) and a plan view of the workpiece (below) to show a keyhole 11 and a measuring beam 13 during welding in accordance with embodiments of the present disclosure. FIG. 2 shows distance values (raw data) from a keyhole of an optical coherence tomograph. The laser power was increased linearly with the passage of time, which is why the capillary depth increases.

As shown in FIG. 1, the laser deep welding process produces a vapour capillary or keyhole 11, during a welding process along the beam axis of the processing beam 10, which is surrounded by liquid melt 12. The depth Td of the keyhole, in what follows also called the keyhole depth, is related to the weld seam depth or weld penetration depth Te. As viewed in the feed direction 20, the solidified melt 14 is located behind the liquid melt 12.

To determine the welding depth, or in particular the depth of the keyhole 11, for example during the welding process, the measuring beam 13 of an optical coherence tomograph may be superimposed coaxially with the processing beam 10, and focussed into the opening of the keyhole 11. The incident light hits the floor, or the end, of the keyhole 11, is partially reflected there, and returns to the optical coherence tomograph, with the aid of which the depth Td of the keyhole 11 may be measured with high precision.

Since coherence tomography is an optical measurement method, the measurement is based on the back reflection of light from the end of the keyhole 11. Since the keyhole 11 is usually small in diameter and very pointed, the measurement light in the keyhole 11 is reflected very poorly, so that very little light is reflected back from the object arm of the interferometer. In particular in the case of high feed rates the keyhole 11 is also strongly curved.

From a welding depth of typically 4-6 mm upwards, the number of valid distance measurements from the keyhole floor decreases rapidly (see right-hand region in FIG. 2). It is then no longer possible to monitor/control the welding depth with a conventional OCT sensor. Typically, valid measurement data at every 0.1 mm interval of the welding feed are advantageous in order to achieve complete quality assurance. At a welding speed of 6 m/min (=100 mm/s), for example, this interval is covered in 1 ms. A typical sensor has a measuring rate of 70 kHz and therefore completes 70 measurements during this time period.

There are various reasons for the low measurement yield with a large welding depth:
1) With a large welding depth, the keyhole at the keyhole floor tapers down to a tube of a few μm diameter. Even with good focusing of the measuring light, only a fraction of the light reaches the keyhole floor in its original state, i.e. with no or few reflections from the keyhole wall.
2) The keyhole fluctuates at approx. 100-1000 kHz in its position, width and depth, as well as in the straightness of its profile. The transmission of light forwards and backwards with few reflections from the keyhole wall becomes increasingly rare.
3) The alteration of the depth of the keyhole floor during an illumination cycle smears the interference fringes, as a result of which the signal strength is reduced.
4) In part, the polarisation direction of the keyhole reflex is rotated, so that with a linearly polarised input no interference with the light from the reference arm is possible.
5) Light can be absorbed by the metal vapour in the keyhole.
6) For measurement rates in the MHz range, in order, for example, to execute sequential measurements in the lead-in zone, keyhole and lead-out zone, higher light intensities are required, due to the significantly shorter illumination times.

In order to avoid the above-cited disadvantages, in accordance with the invention an additional element, namely the optical amplifier, is introduced into the beam path in order to amplify the primary beam, the secondary beam, or both beams optically. This enables a low power light source with a broadband spectrum to be used for FD-OCT ("Fourier domain optical coherence tomography" or "optical coherence tomography in the frequency domain"), as a result of which the depth of a keyhole can be determined reliably and with high precision. By virtue of the optical amplification, deeper vapour capillaries can, in particular, still be measured. With a light source with a broadband spectrum, such as a superluminescent diode or a supercontinuum source, optical frequency domain coherence tomography, in particular optical spectral domain coherence tomography (spectral domain OCT), can be used for measurement. Alternatively, with a monochrome light source with a periodically tuned wavelength, a so-called swept source OCT measurement method can be used. Here the primary light can be amplified e.g. with a semiconductor-based optical amplifier.

In one embodiment, the amount of light entering the keyhole can be increased by a factor of 10 from approx. 50 mW to approx. 500 mW by means of an optical amplifier. This enables the tenfold-reflected measuring light to enter a detection device, and the signal strength of the light reflected from the keyhole can be increased by a factor of 3.16. Here it is noted that the signal strength can be assumed to be proportional to the square root of the product of the intensities of the reference light and the reflected measuring light: sqrt (I_ref*I_mess). This means that the measurement signal is clearly above the noise that is caused by the dark noise of the detection device. If the additional noise in the OCT measurement signal due to ASE, i.e. by spontaneously emitted radiation, is amplified by less than a factor of 3.16, an improved signal-to-noise ratio can be achieved.

In a further embodiment, the primary beam, i.e. the measuring beam, may firstly be amplified and then divided into a multiplicity of primary beams. The multiplicity of primary beams may then be directed onto the workpiece so that at least one of the primary beams hits the keyhole precisely, despite fluctuations in the keyhole. The primary beam may be divided into a multiplicity of primary beams by using a multi-core fibre that has a plurality of channels. Alternatively, the amplified primary beam may be fanned out, e.g. by means of a lens, and then bundled into a multiplicity of primary beams by means of a micro-lens arrangement. The proportion of measuring light that enters the keyhole may be increased by a beam splitter, such as a twin-spot beam splitter, at the expense of the proportion of measuring light that hits the workpiece surface.

Figure 3:
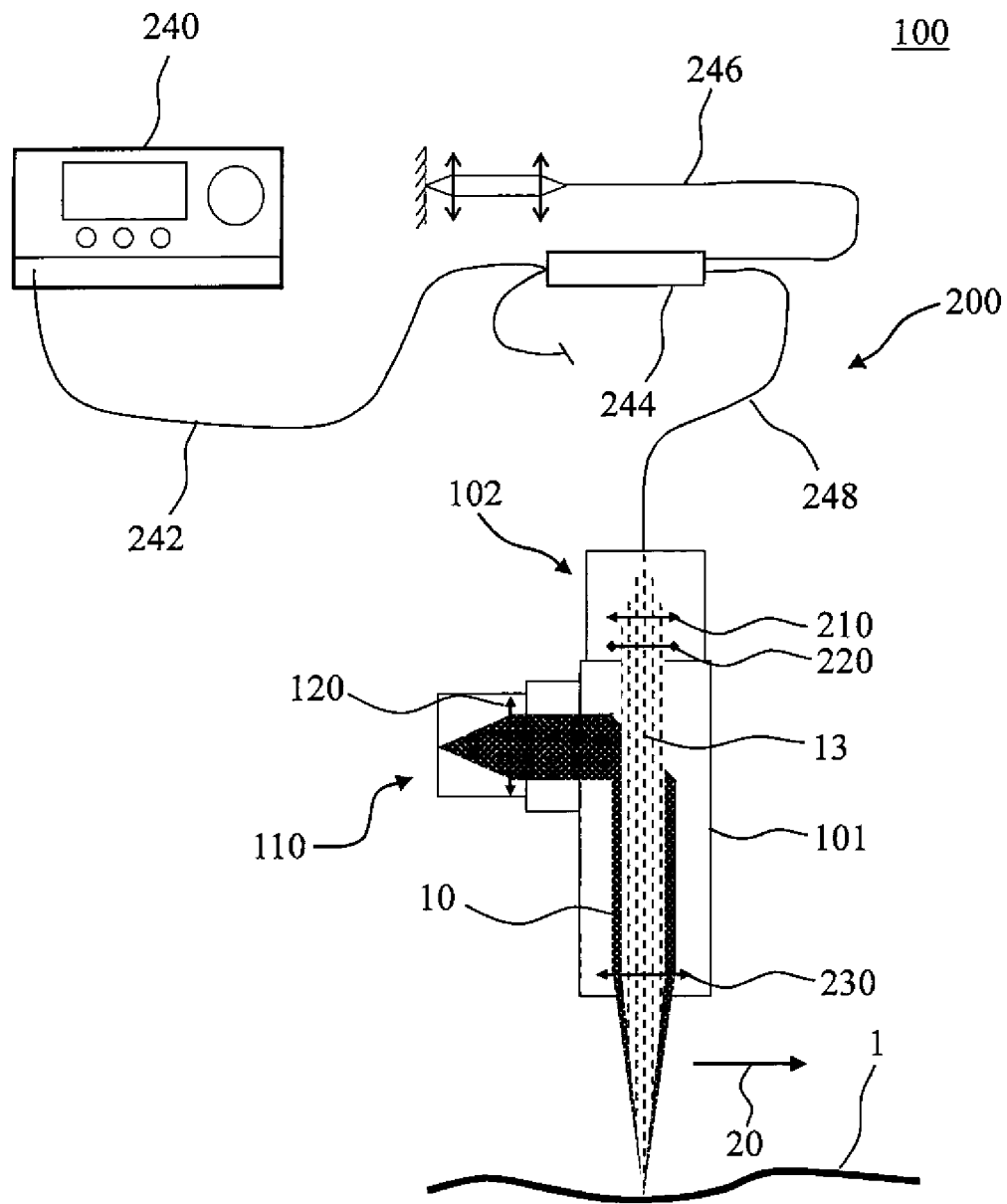
FIG. 3 shows a schematic representation of a laser processing system in accordance with embodiments of the present disclosure.

FIG. 3 shows a schematic representation of a laser processing system 100 in accordance with embodiments of the present disclosure, The laser processing system 100 comprises a laser processing head 101, and in particular a laser welding head for deep laser welding.

The laser processing system 100 may comprise a laser device 110 for generating a processing beam 10 (also referred to as a "laser beam" or a "processing laser beam"). The laser processing system 100 also comprises the distance-measuring device 200, in particular for depth measurement of a keyhole during laser welding, in accordance with the embodiments described here. The laser processing head 101 is configured to direct the processing beam 10 onto a processing region of a workpiece 1. The laser processing head 101 may have a collimator lens 120 for the collimation of the processing beam 10.

The distance-measuring device 200 generates the primary beam, which is directed onto the workpiece, and in particular into the keyhole. The primary beam may also be referred to as the "measuring beam", or the "optical measuring beam". The fraction of the measuring beam reflected from the keyhole floor, for example, is referred to as the "secondary beam".

The distance-measuring device 200 typically comprises collimator optics 210, which are configured to collimate the optical measuring beam 13 (primary beam), deflection optics 220 to deflect the collimated optical measuring beam 13 from an optical axis, and focusing optics 230, which are configured to focus the deflected optical measuring beam 13 onto the workpiece 1.

In some embodiments, the processing beam 10 and the optical measuring beam 13 may be coaxial in at least some sections, and in particular may be coaxially superimposed in at least some sections. The device 200 may, for example, be configured to couple the optical measuring beam 13 into a beam path of the laser processing head 101. The merger of the optical measuring beam 13 and the processing beam 10 may take place downstream of the deflection optics 220 and upstream of the focusing optics 230.

In typical embodiments, which may be combined with other embodiments described here, the collimator optics 210, the deflection optics 220 and the focusing optics 230, are integrated into the welding head 101. The welding head 101 may, for example, comprise a collimator module 102 that is integrated into the welding head 101, or mounted on the welding head 101. The collimator module 102 may comprise the collimator optics 210 and the deflection optics 220. The focusing optics 230 may be optics, such as a focusing lens, that are common to the processing beam 10 and the measuring beam 13.

The laser processing system 100, or parts thereof, such as the welding head 101, may be moved along a processing direction 20 in accordance with some embodiments. The processing direction 20 may be a cutting direction and/or a movement direction of the laser processing system 100, such as the welding head 101, with respect to the workpiece 1. In particular, the processing direction 20 may be a horizontal direction. The processing direction 20 may also be referred to as the "feed direction".

In typical embodiments, the determination or measurement of the depth of the keyhole in real time is based on the principle of optical coherence tomography, which makes use of the coherence properties of light with the aid of an interferometer. In particular, the device 200 may comprise a coherence interferometer or an optical coherence tomograph. The device 200 may comprise an evaluation unit 240 and (or with) a broadband light source (e.g. a superluminescent diode, SLD), which couples the primary beam into an optical waveguide 242. In a beam splitter 244, which preferably has a fibre coupler, the measuring light is split into a reference arm 246 and an object arm (also referred to as a "measuring arm"), which leads via an optical waveguide 248 into the welding head 101. The device 200 also comprises the optical amplifier so as to amplify the primary beam, the secondary beam, or both beams, so that even deep keyholes can be measured reliably and accurately.

The collimator optics 210 (also called the "collimator module") serve to collimate the measuring light (primary beam/optical measuring beam 13) emitted from the optical waveguide 248. In accordance with some embodiments, the optical measuring beam 13 in the welding head 101 may be coaxially superimposed with the processing beam 10. The processing laser beam 10 and the optical measuring beam 13 may then be focused on the workpiece 1 by means of the focusing optics 230, which may be a common lens or a focusing lens. Here the focus position and focus diameter of the optical measuring beam 13 may be adjusted by the deflection optics 220 such that the measuring light is directed into the keyhole. The measuring light reflected back from the keyhole, that is to say, the secondary beam, is imaged by the focusing optics 230 onto the exit/entrance surface of the optical waveguide 248, superimposed in the fibre coupler 244 with the light reflected back from the reference arm 246, and then directed back into the evaluation unit 240. The superimposed light contains information about the path length difference between the reference arm 246 and the object arm. This information is evaluated in the evaluation unit 240, as a result of which the user obtains information on the distance between the floor of the keyhole and, for example, the welding head 101.

In accordance with some embodiments, the device 200 may be configured to measure a distance to the workpiece 1, for example with respect to a reference point defined by the device 200, by means of the optical measuring beam 10. In particular, the device 200 may be configured to measure a change in distance as the welding head 101 moves along the processing direction 20. This may be used, for example, to create a depth profile of the keyhole. Alternatively, or in addition to the measurement of the depth of the keyhole, a topography measurement of the workpiece 1, for example of the weld seam, may be carried out. In accordance with some embodiments the topography measurement may be used for purposes of error detection and/or regulation of one or a plurality of process input variables. The process input variables may comprise e.g. a processing speed, a laser power, a laser focus, and/or operating parameters of the laser processing head.

In some embodiments, a topography measurement may be executed in the region around the processing position. For this purpose, the optical measuring beam 13 may be displaced laterally and height information may be recorded simultaneously. This creates a height profile. Interesting height profiles in laser processing may be, for example, topographies in the lead-in zone at right angles to the feed direction, in order, for example, to detect a butt geometry that is to be welded. Furthermore, a topography running transversely to the feed direction may be measured in the lead-out zone in order to record the height profile of the seam bead created during the welding process.

In accordance with some embodiments of the present disclosure, the impact position of the measuring beam may be displaced during laser processing. The device 200 may, for example, be configured to provide the measuring beam on the workpiece 1 upstream of the processing beam, downstream of the processing beam, or at the location of the processing beam, with respect to a processing direction 20 of the processing beam. Possible measuring positions comprise, for example: as viewed in the feed direction of the high-energy processing beam, upstream of processing, in the processing region, and downstream of processing. Furthermore, the optical measuring beam 13 during processing may be displaced transversely and longitudinally relative to the feed direction through the point of impact of the high-energy processing beam. In this manner it is possible to create depth profiles of the vapour capillaries occurring during processing with a high-energy processing beam.

As has been explained with reference to FIGS. 1 and 2, conventional measurements of the keyhole depth experience problems with fluctuation of the position and depth of the keyhole, keyhole narrowness and curvature, depolarisation of the keyhole reflex, light absorption by metal vapour, and shorter illumination time at higher measurement rates.

Figure 4:
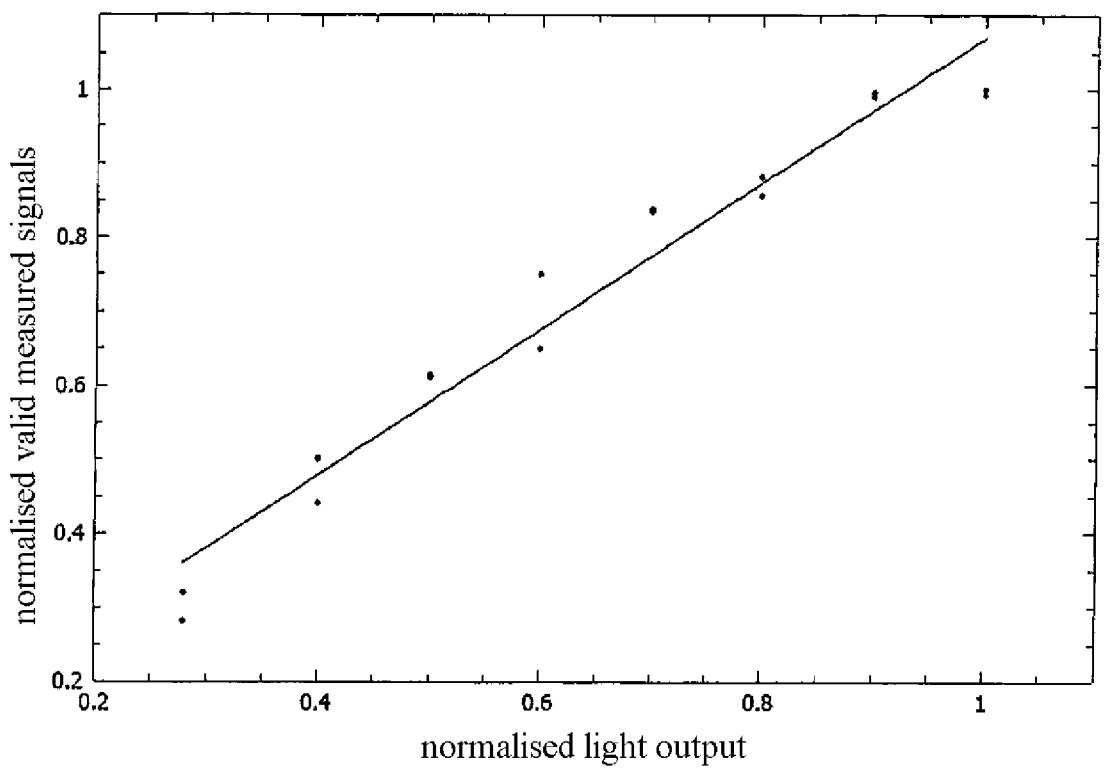
FIG. 4 shows the increase in valid measured values from a keyhole with increasing light output from the source.

To solve the above problems it is advantageous to increase the amount of light. FIG. 4 shows the increase in valid measured values from a keyhole with increasing light output of the light source of an FD-OCT system. In all measurements the keyhole had the same depth. An approximately linear relationship may be seen in the power range shown. It may be assumed that with increasing power the number of valid measured values from the keyhole continues to increase. Conversely, deeper vapour capillaries may also be measured with a higher light output, as a sufficient number of valid measured values is then still available.

The Fourier domain (frequency domain) optical coherence tomography (FD-OCT) enables the use of broadband light sources that possess a certain spectral width and nevertheless emit coherent light. Here, for example, superluminescent diodes (SLDs) may be used. Coherent light is required so as to produce interference effects when superimposing light from the object and reference arms of the interferometer. The spectral bandwidth is required to achieve sufficient axial resolution. This is given by:

$$\Delta z = 2 \ln(2) \lambda_0^2 / (\pi \Delta \lambda) \qquad \text{Equation (1)}$$

$\Delta z$ specifies the axial resolution, $\lambda^0$ the central wavelength, and $\Delta \lambda$ the full spectral bandwidth at the half-height of the spectrum (FWHM) (assumption: Gaussian spectrum).

Lasers are therefore ruled out for FD-OCT due to the small line width. Light emitting diodes (LEDs) and other broadband light sources possess too small a coherence length. The maximum achievable output power of SLDs is in general limited to a few tens of milliwatts, or a few 100 milliwatts, depending on the emission wavelength. If SLDs were operated at higher currents to achieve higher output powers, the SLD would switch to laser operation, significantly reducing the spectral bandwidth and thus losing the axial resolution of the OCT system. This means that no powerful light sources are available for measuring the welding depth with the aid of FD-OCT in order to compensate for the large losses that occur in the keyhole.

The combination of light from a plurality of light sources to improve performance, as is often the case with LEDs, is not an alternative because only light from the same source may interfere with itself. With two different SLDs, the phases of the two light waves do not match. One field of application for optical coherence tomography is medical technology, and in particular the examination of the interior of the eye. To avoid damage to the eye during the examination, the light output must be low so that in this field there is no need to develop OCT systems with high output. Also for the pure topography measurement no powerful light sources are necessary, because surfaces, even if they are strongly scattering or absorbing, still reflect back sufficient light for a distance measurement. Scattered light from a surface is significantly more intense than the light reflected back from the keyhole.

In accordance with the invention, the problem of too low a light output reflected back from the keyhole is solved by providing an additional element, namely the optical amplifier. The optical amplifier may be located at different positions in the inventive device to amplify the primary beam, the secondary beam, or both beams optically. The light source and the optical amplifier may be separate elements.

On the one hand, the light arriving from the light source may be amplified, so that more light is directed into the keyhole, and consequently more light is reflected back. On the other hand, the weak light reflected back from the keyhole may be amplified before it is spectrally split in the spectrometer and spatially distributed to the detector row, further reducing the light output per detector pixel.

Various embodiments for the light amplification task are explained in what follows.

Figure 5:
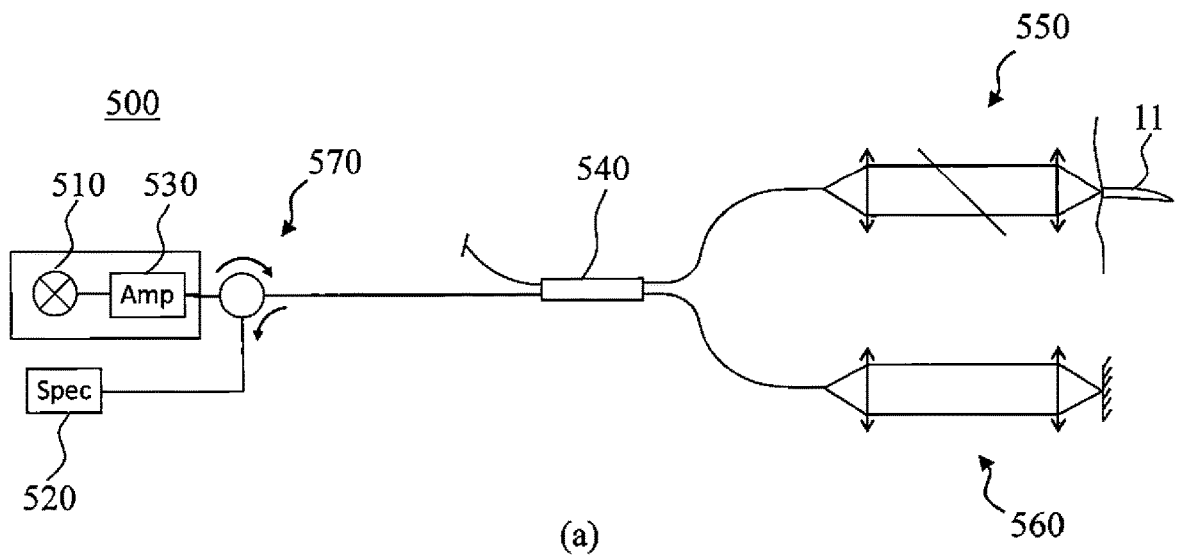
FIG. 5 shows a schematic representation of a distance-measuring device for a laser processing system in accordance with embodiments of the present disclosure.
Figure 5:
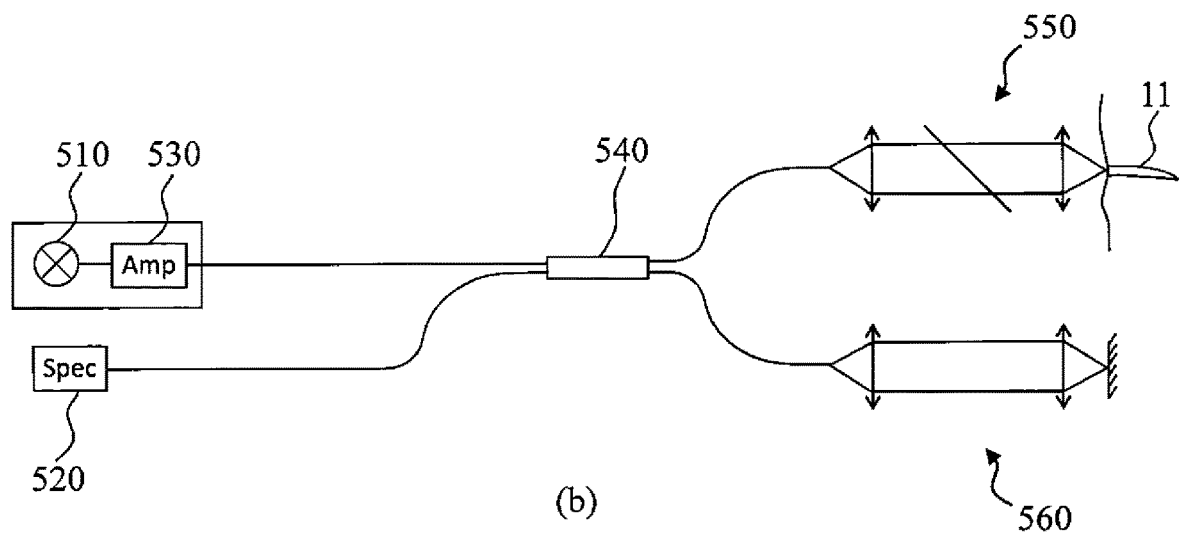

FIG. 5 shows a schematic representation of a distance-measuring device 500 for a laser processing system in accordance with embodiments of the present disclosure. In the device 500 in FIG. 5, the light source is amplified.

The device 500 comprises a light source 510 configured to generate a primary beam that is to be directed onto a workpiece, at least one detection device 520 configured to record a secondary beam reflected from the workpiece, at least one optical amplifier 530 configured to amplify the primary beam and/or the secondary beam, and an evaluation unit configured to evaluate interference between spectral components in the frequency domain. The device 500 may be an optical coherence tomograph for the frequency domain (FD-OCT). The detection device 520 and the evaluation unit may be integrated in one system component. For example, the detection device 520 and the evaluation unit may form a spectrometer.

A distance-measurement method for a laser processing system using the device 500 comprises a direction of the primary beam onto the workpiece, a direction of the secondary beam from the workpiece towards the detection device, an optical amplification of the primary beam and/or the secondary beam, and an evaluation of interference between spectral components in the frequency domain. The method may further comprise the determination of a depth or depth profile of the keyhole 11 on the workpiece, and/or a topography of the workpiece, using the secondary beam reflected from the workpiece.

In accordance with some embodiments, which may be combined with other embodiments described here, the light source 510 may comprise, or be, a superluminescent diode (SLD) or a supercontinuum source. Typically, the at least one optical amplifier 530 may be a doped fibre amplifier (DFA), a semiconductor-based optical amplifier (SOA), a Raman amplifier, an optical parametric amplifier (OPA), a bi-directional amplifier, or a combination of these.

The light source 510 and the at least one optical amplifier 530 may be arranged sequentially such that the primary beam is directed into the at least one optical amplifier 530. For example, the at least one optical amplifier 530 may be arranged in the beam path of the primary beam such that the primary beam is directed directly from the light source 510 into the at least one optical amplifier 530. The intensity of the light source 510 may be adjusted such that the amplifier 530 is operated at the optimum operating point and thus delivers an optimum signal-to-noise ratio. One cause of noise in an amplifier is amplified spontaneous emission (ASE) due to excited charge carriers that spontaneously enter the ground state, thereby emitting a photon that is amplified by the other excited charge carriers in the amplifier medium.

There are various setting parameters for purposes of reducing the ASE, that is to say, optimising the signal-to-noise ratio. On the one hand, the amplifier medium itself may be varied. Thus compared to semiconductor-based amplifiers, fibre amplifiers often have a longer-life excited state, which is why fewer charge carriers spontaneously switch to the ground state, resulting in lower ASE. Furthermore, the pumping power of the amplifier may be influenced (in the case of optically pumped amplifiers, also the pump wavelength). Moreover, the light output from the light source to be amplified that enters the amplifier influences the ASE. In addition, the amplifier design may be optimised for the respective application.

In accordance with some embodiments, the device 500 comprises a beam splitter 540 to provision an object arm 550 and a reference arm 560. The beam splitter 540 preferably has a fibre coupler, so that the primary beam is split into the reference arm 560 and the object arm 550, which leads, for example, via an optical waveguide into the welding head.

In some embodiments, as shown in FIG. 5(a), the device 500 comprises at least one circulator 570, which is configured so as to provision two or more beam paths for the primary beam and/or the secondary beam. In particular, the circulator 570 may be configured to separate the forward and return light waves. FIG. 5(b) shows a simplified design of the device without a circulator.

In the present embodiment, the light output in both the object arm and the reference arm is amplified. It is therefore advantageous that the back reflection from the reference arm 560 is so low that the detection device 520, which may be a spectrometer, does not overload. This may be achieved either by an adapted coupling ratio between the object arm and the reference arm (less light in the reference arm) or by attenuation in the reference arm 560. In the case of fibre amplifiers, the light output may be increased by more than two orders of magnitude.

Figure 6:
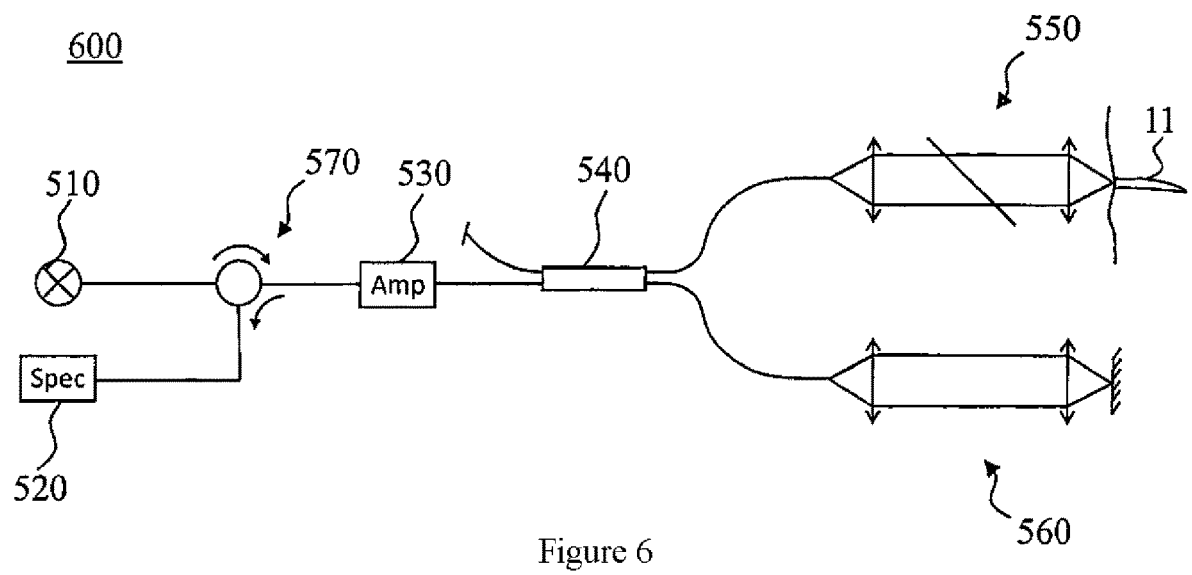
FIG. 6 shows a schematic representation of a distance-measuring device for a laser processing system in accordance with further embodiments of the present disclosure.
Figure 7:
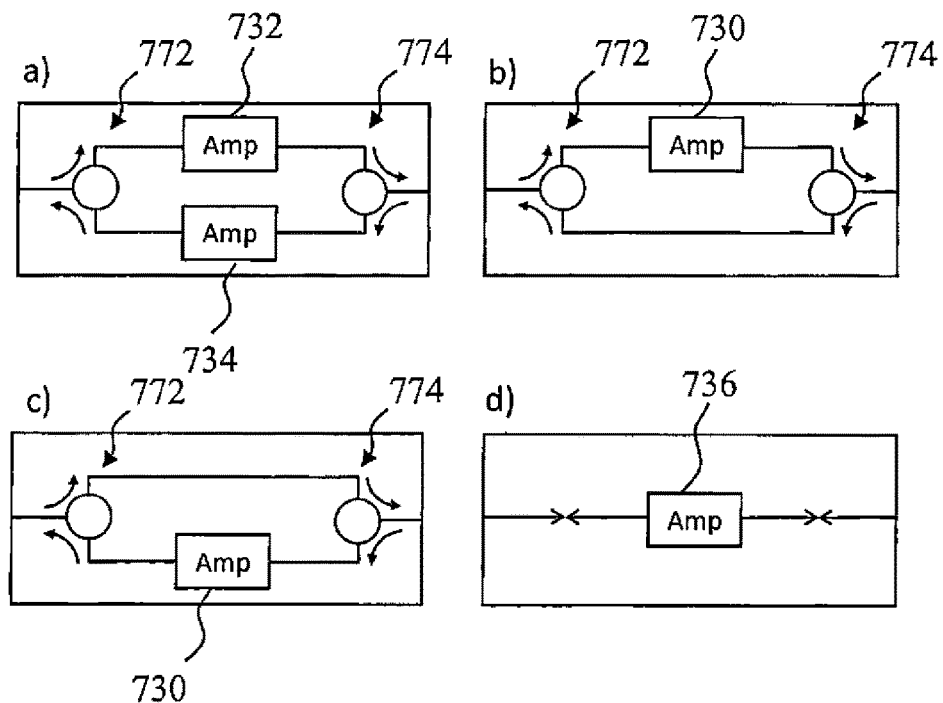
FIG. 7 shows options for the deployment of an amplifier in a fibre that is used for both the forward and return transport of the light.

FIG. 6 shows a schematic representation of a distance-measuring device 600 for a laser processing system in accordance with further embodiments of the present disclosure. In the device 600 of FIG. 6, amplification takes place in the fibre that connects the light source or spectrometer and the object or reference arm ("common path fibre"). FIG. 7 shows options for the deployment of an amplifier in a fibre that is used for both the forward and return transport of the light, In accordance with some embodiments, at least one optical amplifier 530 is arranged in a beam path common to the primary beam and the secondary beam, such as on a fibre connecting the light source or spectrometer and the object or reference arm.

The device 600 may comprise a beam splitter 540 to provision the object arm 550 and the reference arm 560. Typically, the device 600 comprises at least one circulator 570, which is configured so as to provision two or more beam paths for the primary beam and the secondary beam. The at least one optical amplifier 530 may be arranged between the circulator 570 and the beam splitter 540. The at least one circulator 570 may be further arranged so as to direct the primary beam into the at least one optical amplifier 530, and to direct the secondary beam towards the detection device 520, such as the spectrometer.

In accordance with the present embodiment, the light passes through the amplifier at this point on both the forward path and also the return path. The amplifier may, for example, be operated bi-directionally, as shown in the example in FIG. 7d). Fibre amplifiers are not designed for bi-directional operation. Here, therefore, with the aid of circulators, the light may be amplified separately on the outward and/or return path.

In accordance with some embodiments, the at least one circulator may comprise a first circulator 772 and a second circulator 774, wherein the at least one optical amplifier is arranged between the first circulator 772 and the second circulator 774. In FIGS. 7a)-c) a first beam path is provided for the primary beam and a second beam path for the secondary beam between the first circulator 772 and the second circulator 774.

In the example of FIG. 7a), the at least one optical amplifier comprises a first optical amplifier 732 and a second optical amplifier 734, wherein the first optical amplifier 732 is arranged in the first beam path and the second optical amplifier 734 is arranged in the second beam path. In other words, separate amplifiers are provided for the forward and return paths.

In accordance with further embodiments, the at least one optical amplifier 730 may be arranged in the first beam path or in the second beam path. In FIG. 7b), the at least one optical amplifier 730 is arranged in the first beam path. In other words, (only) the primary beam is amplified, i.e. amplification takes place only on the forward path. In FIG. 7c), the at least one optical amplifier 730 is arranged in the second beam path. In other words, (only) the secondary beam is amplified, i.e. amplification takes place only on the return path.

In other embodiments, a single beam path is provided for the primary beam and the secondary beam between the circulator and the beam splitter, wherein the at least one optical amplifier is a bi-directional optical amplifier 736. This is illustrated in an exemplary manner in FIG. 7d).

Figure 8:
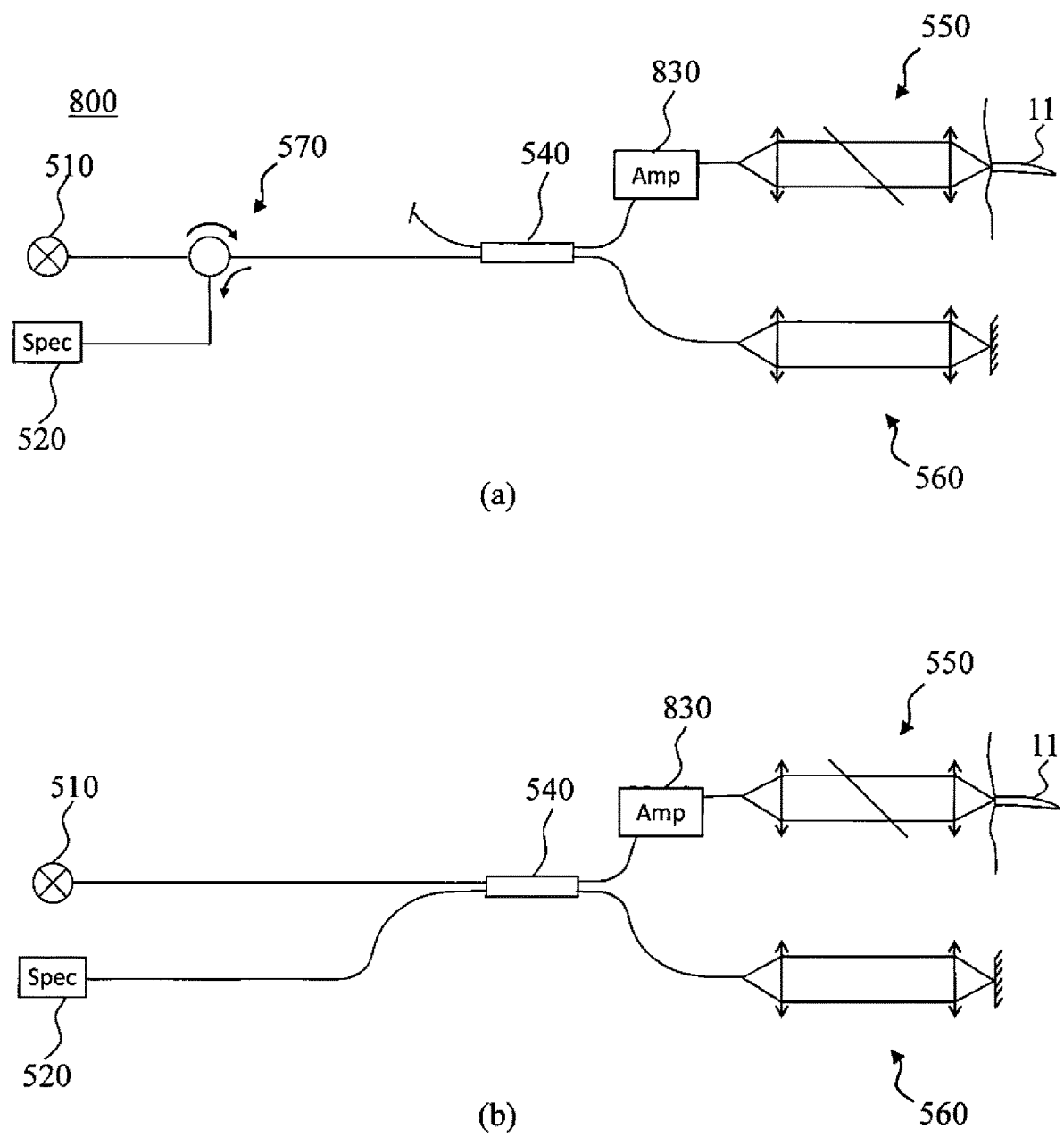
FIG. 8 shows a schematic representation of a distance-measuring device for a laser processing system in accordance with further embodiments of the present disclosure.

FIG. 8 shows a schematic representation of a distance-measuring device 800 for a laser processing system in accordance with further embodiments of the present disclosure. In the device 800 of FIG. 8 amplification takes place in the object arm 550. FIG. 8(a) shows a device 800 with a circulator 570. FIG. 8(b) shows a simplified device without a circulator.

The device 800 comprises the beam splitter 540 to provision the object arm 550 and the reference arm 560. The at least one optical amplifier 830 may be arranged in a beam path of the object arm 550. If the amplification takes place in the object arm 550, the forward and return light waves may also be taken into account here. For example, the embodiments shown in FIG. 7 are available, which may be combined with the embodiment described here.

An alternative build may also be used for amplification in the object arm, which also permits separate amplification of the forward and/or return light waves. In addition, a second spectrometer may be used to enable a simultaneous evaluation of the spectral form of the light distribution. Examples for this purpose are shown in FIG. 9.

In accordance with some embodiments, the device 900 comprises a first spectrometer 920 and a second spectrometer 922. The first spectrometer 920 and the second spectrometer 922 may each comprise a detection device and an evaluation unit in accordance with the present disclosure. The device 900 may also comprise a first beam splitter 940 and a second beam splitter 942. The first beam splitter 940 may provision the object arm 550 and the reference arm 560. Typically, the first beam splitter 940 is located between the light source 510 and at least one circulator 970. The at least one circulator 970 may be arranged in the beam path of the object arm 550. The second beam splitter 942 may be connected to the first spectrometer 920, the second spectrometer 922, the reference arm 560 and the circulator 970 (for example via at least one optical amplifier 930).

Figure 9:
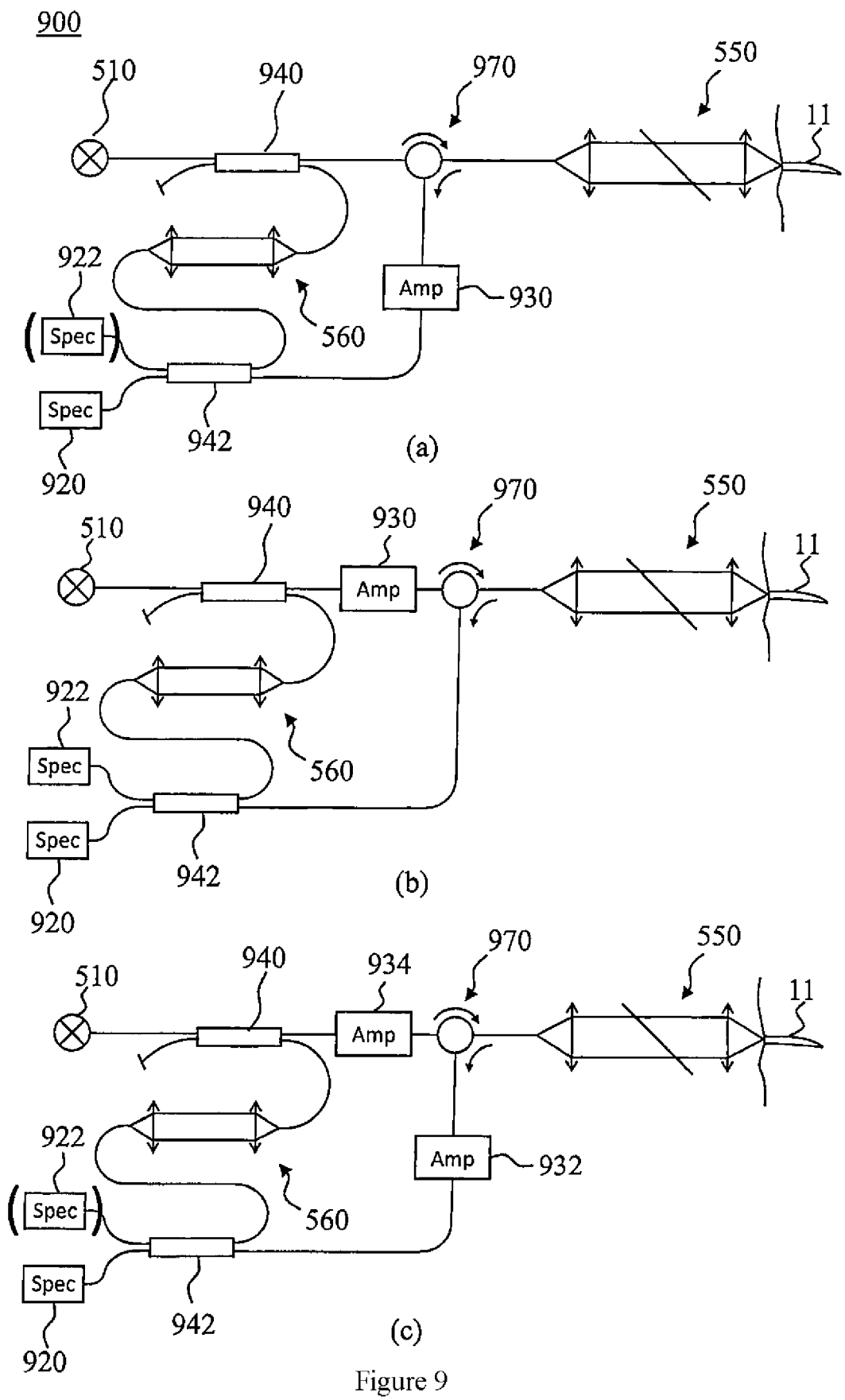
FIG. 9 shows alternatives for the amplification in the object arm.

In the example of FIG. 9(*a*), the at least one optical amplifier 930 is arranged between the at least one circulator 970 and the detection device (that is to say, the first spectrometer 920 and second spectrometer 922). In particular, the at least one optical amplifier 930 may be arranged between the at least one circulator 970 and the second beam splitter 942. In the example of FIG. 9(*b*), the at least one optical amplifier 930 is arranged between the at least one circulator 970 and the first beam splitter 940.

With respect to FIG. 9(*c*), the at least one optical amplifier comprises a first optical amplifier 932 and a second optical amplifier 934. The first optical amplifier 932 is arranged between the at least one circulator 970 and the detection device (that is to say, the first spectrometer 920 and second spectrometer 922). The second optical amplifier 934 is arranged between the first beam splitter 940 and at least one circulator 970.

Figure 10:
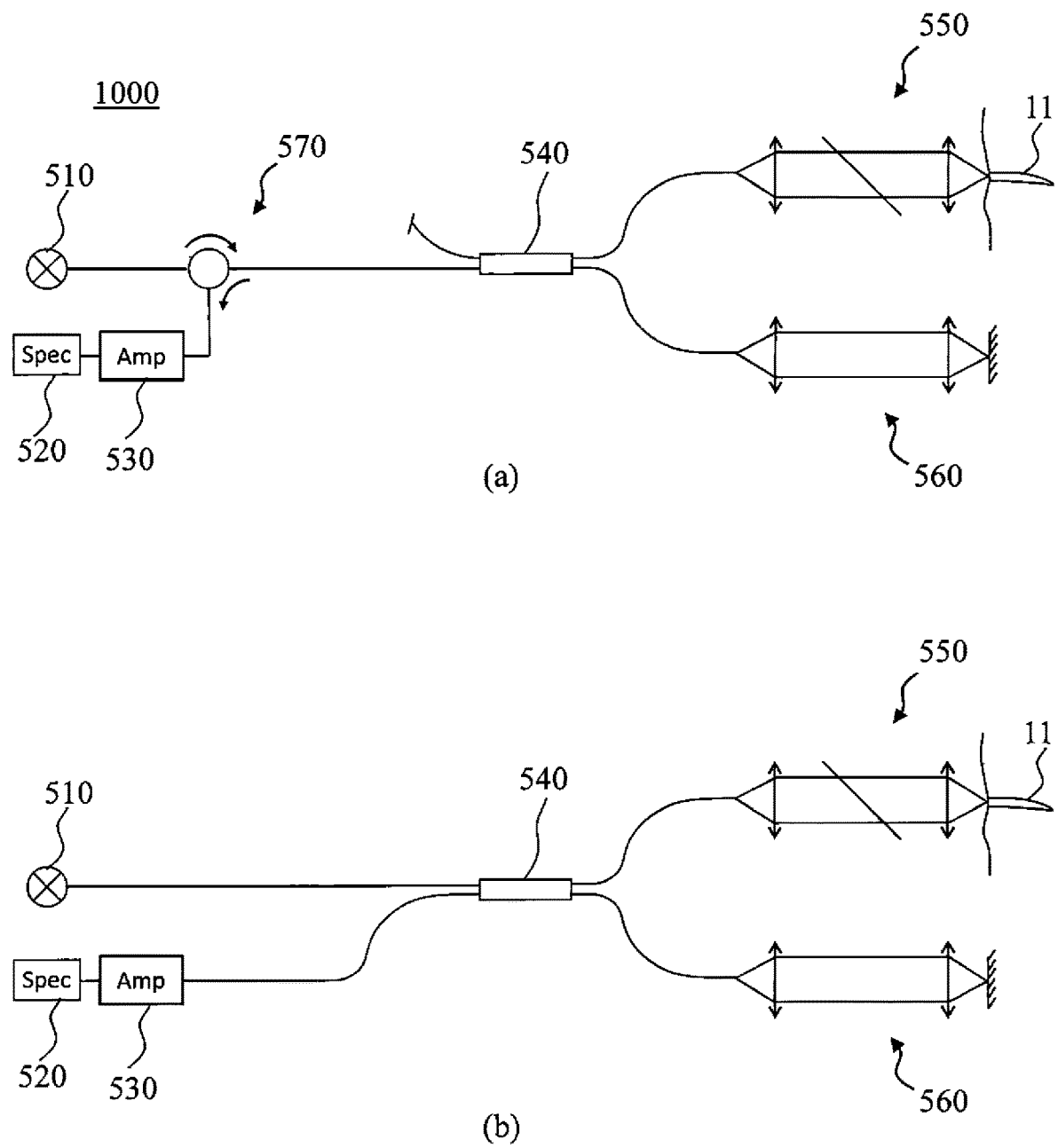
FIG. 10 shows a schematic representation of a distance-measuring device for a laser processing system in accordance with further embodiments of the present disclosure.

FIG. 10 shows a schematic representation of a distance-measuring device 1000 for a laser processing system in accordance with further embodiments of the present disclosure. In the device in FIG. 10, an amplification takes place upstream of detection. In particular, the returning light wave modulated by the object arm and reference arm is amplified. FIG. 10(*a*) shows a device with a circulator 570. FIG. 10(*b*) shows a simplified device without a circulator.

In accordance with some embodiments, the at least one optical amplifier 530 is arranged in the beam path of the secondary beam, such that the amplified secondary beam is directed towards the detection device 520. In the example FIGS. 10(*a*) and (*b*), the at least one optical amplifier 530 is arranged between the circulator 570 and the detection device 520.

In accordance with the present embodiment, the amplification may take place immediately before detection, that is to say, immediately upstream of the spectrometer. The light wave modulated by the object and reference arm is amplified. If the light enters the spectrometer without amplification, it is spectrally split and distributed, for example, to 256, 512, 1024 or 2048 pixels. This means that the low intensity is distributed over a large number of detector pixels, and therefore only a small fraction of the original light is available per detector pixel. Thus, on the detector the threshold is quickly reached at which the signal may no longer be distinguished from the detector noise.

In comparison, the full intensity returning from the object arm and reference arm is still available at the amplifier. An amplifier also has a threshold for incoming light, which is necessary for low-noise amplification. However, since the light has not yet been spectrally split when entering the amplifier, this threshold may be significantly higher than the detector pixel threshold. If the threshold for the amplification of the light in the amplifier is selected appropriately (for example, by an adjusted pump power or amplifier design), only the intensity maxima of the modulated light are significantly amplified, as a result of which the interference pattern is more pronounced and may therefore be better evaluated in the spectrometer. Signal evaluation is still possible even with unfavourable keyhole shapes or large depths, as a result of which very little light is available from the object arm. If the saturation behaviour of the amplifier is also selected appropriately, the spectrometer is not overloaded if, for example, a very good reflecting surface is measured next to the keyhole.

Figure 11:
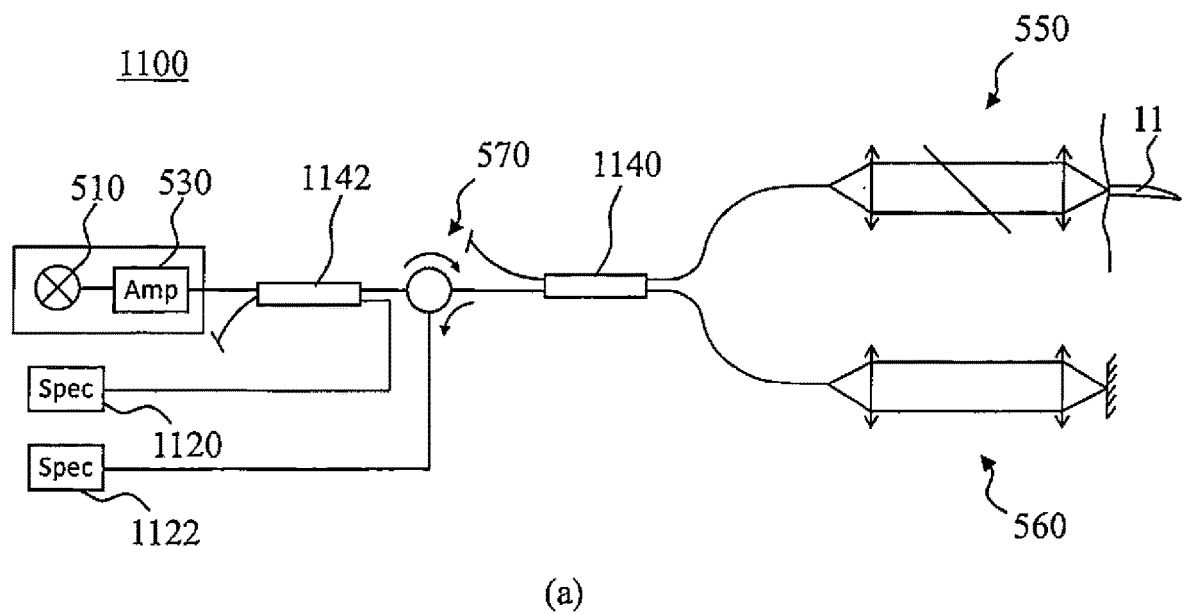
FIG. 11 shows a device for recording a spectral intensity distribution of a light source.
Figure 11:
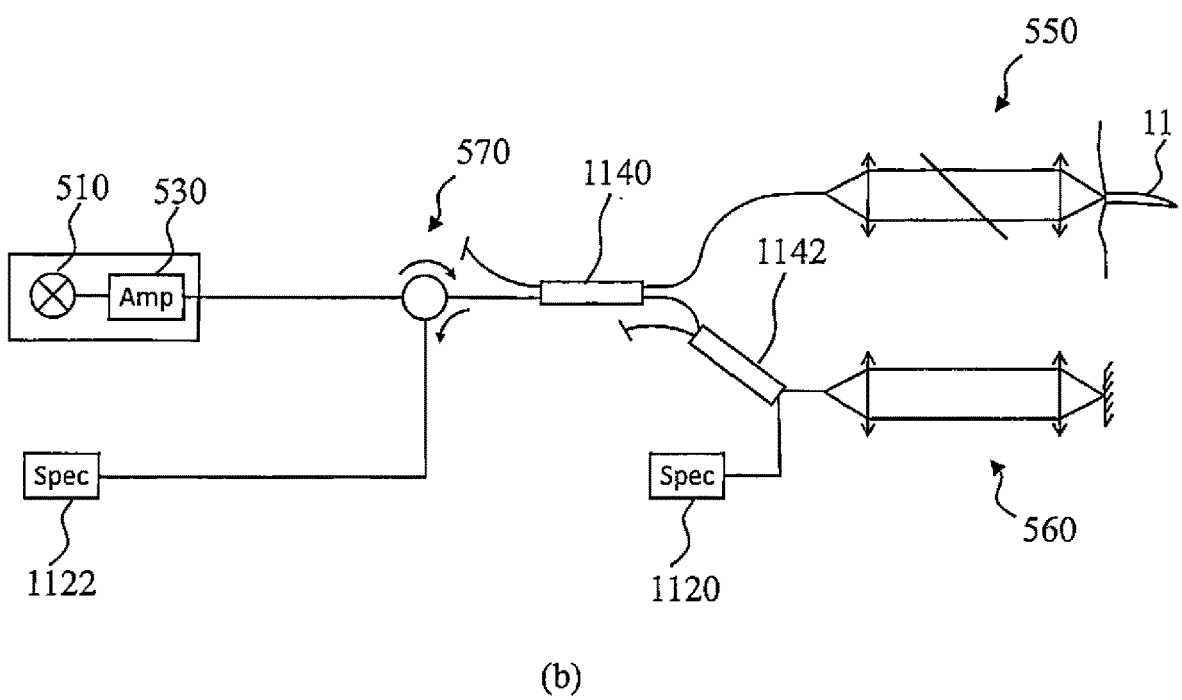

FIG. 11 shows a schematic representation of a device 1100 for a laser processing system in accordance with further embodiments of the present disclosure. A spectral intensity distribution is recorded in the device in FIG. 11. FIG. 11(*a*) shows a recording immediately after amplification. FIG. 11(*b*) shows a recording in the reference arm 560.

With FD-OCT it may be necessary to know the spectral intensity profile of the light source. The emitted spectrum is typically not spectrally flat, but has a maximum in the central region. Before the Fourier transformation of the detected interference pattern, the spectrum may be corrected such that, apart from the interference structure, it is spectrally flat. For this purpose the spectral intensity profile of the light source is required. If the profile remains constant over time, the profile may be recorded and stored just once. However, if the profile changes over time, it is advantageous to record the spectral form during each measuring cycle. FIG. 11 shows two examples of ways of detecting the spectral intensity profile emitted by the light source during each measuring cycle.

In accordance with some embodiments, which may be combined with other embodiments described here, the at least one detection device comprises a first detection device (that is to say, a first spectrometer 1120) and a second detection device (that is to say, a second spectrometer 1122). The device 1100 may also comprise a first beam splitter 1140 and a second beam splitter 1142. The first beam splitter 1140 may be configured so as to provision the object arm 550 and the reference arm 560. The first beam splitter 1140 may be further configured to direct at least a fraction of the secondary beam, for example via the circulator 570, into the second detection device (that is to say, the second spectrometer 1122). The second beam splitter 1142 may be configured to direct at least a fraction of the primary beam into the first detection device (that is to say, the first spectrometer 1120). The circulator 570 may be arranged between the at least one optical amplifier 530 and the first beam splitter 1140. The circulator 570 may be configured to direct at least a fraction of the secondary beam into the second detection device (that is to say, the second spectrometer 1122).

In the example of FIG. 11(*a*), the second beam splitter 1142 is arranged in the beam path of the primary beam. In particular, the second beam splitter 1142 may be arranged between the circulator 570 and the light source 510 (or between the circulator 570 and the optical amplifier 530).

In the example of FIG. 11(*b*), the second beam splitter 1142 is arranged in the reference arm 560. In particular, the second beam splitter 1142 may be arranged between the first beam splitter 1140 and the first detection device (that is to say, the first spectrometer 1120).

In accordance with the invention, an additional element, namely the optical amplifier, is introduced into the beam path in order to amplify the primary beam, the secondary beam, or both beams optically. This enables a low-power broadband light source to be used for FD-OCT ("Fourier domain optical coherence tomography" or "optical coherence tomography in the frequency domain"), which enables the depth of a keyhole to be determined reliably and with high precision. In particular, by means of the optical amplification, deeper vapour capillaries may also be measured.

The amplified amount of light may, on the one hand, be used to increase the measurement frequency, so that more measurements may be performed per unit of time, and thus more data are available for statistical evaluation. In addition, an illumination time may be shortened. Any influence of an axial movement of the keyhole floor on the spectral modulation and any resulting smearing or blurring of the spectral modulation is reduced. On the other hand, the amplified amount of light may be used to increase the amount of measuring light in the object arm, in particular the fraction of measuring light entering the keyhole.

What is claimed is:

1. A distance-measuring device for a laser processing system, comprising:
    a light source configured to generate a measuring beam for direction onto a workpiece;
    at least one detection device configured to detect a reflected part of the measuring beam reflected from the workpiece;
    a beam splitter configured to provide the measuring beam into an object arm and a reference arm;
    at least one circulator configured to direct the measuring beam from the light source into a common beam path between the beam splitter and the at least one circulator and to direct the reflected part of the measuring beam from the common beam path to the at least one detection device; and
    an optical amplifier arranged in the common beam path between the beam splitter and the at least one circulator, the common beam path transmitting the measuring beam from the circulator to the beam splitter for directing the measuring beam into the object arm and towards the workpiece and transmitting the reflected part of the measuring beam reflected from the workpiece to the at least one circulator for directing the reflected part of the measuring beam towards the at least one detection device, the optical amplifier configured to amplify the measuring beam before the measuring beam is directed onto the workpiece and to amplify the reflected part of the measuring beam before the reflected part is directed towards the at least one detection device.

2. The device in accordance with claim 1, wherein the light source comprises at least one superluminescent diode, or a supercontinuum source.

3. The device in accordance with claim 1, wherein the optical amplifier is a fibre amplifier, a semiconductor-based amplifier, a Raman amplifier, an optical parametric amplifier, a bi-directional amplifier, or a combination of these.

4. The device in accordance with claim 1, further comprising a splitting device for splitting the amplified measuring beam into a plurality of measuring beams,
    wherein the splitting device comprises at least one multi-core fibre, or one micro-lens arrangement.

5. The device in accordance with claim 1, wherein the at least one circulator comprises a first circulator and a second circulator, and wherein the optical amplifier is arranged between the first circulator and the second circulator.

6. The device in accordance with claim 5, wherein a first beam path for the measuring beam and a second beam path for the reflected part of the measuring beam are arranged between the first circulator and the second circulator.

7. The device in accordance with claim 1, wherein the device is configured to determine a depth of a keyhole during a laser welding process.

8. The device in accordance with claim 1, further comprising an evaluation device configured to evaluate interference between spectral components in the frequency domain.

9. A laser processing system comprising:
    a laser processing head for provision of a processing beam, wherein the laser processing head is configured to direct the processing beam onto a processing region of a workpiece; and
    a distance-measuring device for a laser processing system, comprising:
        a light source configured to generate a measuring beam for direction onto a workpiece;
        at least one detection device configured to detect a reflected part of the measuring beam reflected from the workpiece;
        a beam splitter configured to provide the measuring beam into an object arm and a reference arm;
        at least one circulator configured to direct the measuring beam from the light source into a common beam path between the beam splitter and the at least one circulator and to direct the reflected part of the measuring beam from the common beam path to the at least one detection device
        an optical amplifier arranged in the common beam path between the beam splitter and the at least one circulator, the common beam path, the common beam path transmitting the measuring beam from the circulator to the beam splitter for directing the measuring beam into the object arm and towards the workpiece and transmitting the reflected part of the measuring beam reflected from the workpiece to the at least one circulator for directing the reflected part of the measuring beam towards the at least one detection device, the optical amplifier configured to amplify the measuring beam before the measuring beam is directed onto the workpiece and to amplify the reflected part of the measuring beam before the reflected part is directed towards the at least one detection device.

10. The laser processing system in accordance with claim 9, wherein the distance-measuring device further comprising an evaluation device configured to evaluate interference between spectral components in the frequency domain.

* * * * *